United States Patent [19]

Saperstein et al.

[11] Patent Number: 4,978,667
[45] Date of Patent: Dec. 18, 1990

[54] SUBSTITUTED 6H-7,8-DIHYDROTHIAPYRANO(3,2-D)-PYRIMIDINES AS HYPOGLYCEMIC AGENTS

[75] Inventors: Richard Saperstein, Edison; Richard L. Tolman, Warren; Eve E. Slater, Short Hills, all of N.J.

[73] Assignee: Merck & Co., Inc., Rahway, N.J.

[21] Appl. No.: 242,766

[22] Filed: Sep. 12, 1988

Related U.S. Application Data

[63] Continuation of Ser. No. 941,477, Dec. 15, 1986, abandoned.

[51] Int. Cl.$^5$ .......................................... A61K 31/505
[52] U.S. Cl. .................................. 514/258; 514/866
[58] Field of Search ............................... 514/258, 866

[56] References Cited

FOREIGN PATENT DOCUMENTS 724745 5/1969 Belgium .
2119368 11/1983 United Kingdom .

Primary Examiner—Frederick E. Waddell
Attorney, Agent, or Firm—Hesna J. Pfeiffer; David L. Rose

[57] ABSTRACT

There are disclosed certain 2-alkyl-4-substituted 6H-7,8-dihydrothiapyrano[3,2-d]pyrimidines which have oral hypoglycermic activity and with such ability to lower blood sugar are useful in the treatment of type II diabetes and/or obesity with associated insulin resistance. Processes for the preparation of such compounds and compositions containing such compounds as the active ingredient thereof are also disclosed.

2 Claims, No Drawings

SUBSTITUTED 6H-7,8-DIHYDROTHIAPYRANO(3,2-D)-PYRIMIDINES AS HYPOGLYCEMIC AGENTS

This is a continuation of application Ser. No. 941,477, filed Dec. 15, 1986, now abandoned.

BACKGROUND OF THE INVENTION

Certain 6H-7,8-dihydrothiapyrano[3,2-d]-pyrimidines are disclosed in Belgian Patent No. 724745 as intermediates for the preparation of compounds with cardiovascular and coronary dilation activity, however, suggestion is made neither of any hypoglycemic activity nor of weight reducing properties for either the intermediates or the final products. Great Britain No. 2119368 discloses 6H-7,8-dihydrothiapyrano[[3,2-d]pyrimidines with a very different substitution pattern on the nucleus when compared with the instant compounds.

SUMMARY OF THE INVENTION

The instant invention is concerned with 6H-7,8-dihydrothiapyrano[3,2-d]pyrimidines which are useful as hypoglycemic and/or weight reducing agents. Thus, it is an object of this invention to describe such compounds. It is a further object of this invention to describe the hypoglycemic activity of such compounds. A still further object is to describe compositions containing such compounds as the active ingredient thereof Further objects will become apparent from a reading of the following description.

DESCRIPTION OF THE INVENTION

The 2-alkyl-4-substituted 6H-7,8-dihydrothiapyrano[3,2-d]pyrimidines of this invention are known compounds having been disclosed as intermediates in the preparation of cardiovascular agents The compounds with the novel hypoglycemic activity have the following structure:

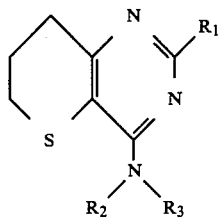

wherein
$R_1$ is hydrogen or loweralkyl of from 1 to 6 carbon atoms;
$R_2$ and $R_3$ are hydrogen or they may be joined to form a heterocycle of 5 members which may also include one or two additional heteroatoms independently selected from nitrogen, lower alkylated nitrogen or oxygen $R_2$ and $R_3$ may be joined to form a heterocycle of 6 members which may also include one additional heteroatom in the 2 or 3 position or 2 additional heteroatoms in any position indepedently selected from nitrogen, lower-alkylated nitrogen or oxygen, or a single heteroatom may be in the 4 position selected from, unsubstituted nitrogen or nitrogen substituted with loweralkyl of 1,2,4,5 or 6 carbon atoms.

The loweralkyl group of this invention may contain from 1 to 6 carbon atoms and may be in either a straight or branched configuration. Exemplary of such groups are methyl, ethyl, propyl, isopropyl, butyl, sec-butyl, pentyl, hexyl, and the like.

The preferred compounds of this invention are those wherein $R_1$ is methyl, ethyl, propyl or isopropyl; and $R_2$ and $R_3$ are joined to form the heterocyclic groups piperazine, N-methylpiperazine, N-ethylpiperazine, and N-propylpiperazine.

The instant compounds are prepared from the appropriate $R_1$ substituted thiapyranopyrimidin-4-one which is treated with phosphorous oxychloride to prepare the analogous 4-chloro compound which, with treatment with the appropriately substituted amine or heterocyclic amine prepares the desired compounds. The general synthetic procedures are described in Belgian Patent No. 724245.

Diabetes is a condition characterized by abnormal insulin secretion and a variety of metabolic and vascular manifestations reflected in a tendency toward inappropriately elevated blood glucose levels and which if left poorly treated or untreated can result in accelerated, nonspecific athersclerosis, neuropathy and thickened capillary lamina causing renal and retinal impairment Diabetes is characterized as being insulin dependent (Type I) and non-insulin dependent (Type II). Type I diabetes is due to damage and eventual loss of the β-cells of the pancretic islets of Langerhans with a resulting loss of insulin production Type II diabetics secrete insulin, however, the insulin is somehow not properly or effectively utilized in the metabolism of blood sugars and glucose accumulates in the blood to above normal levels This condition is termed insulin resistance.

With the certainty of serious complications resulting from high glucose levels in poorly controlled or uncontrolled diabetics, means to lower blood glucose have been research goals for a considerable period of time. With Type I diabetes glucose control can only be achieved with daily insulin injections With Type II diabetes glucose control can be effected from a combination of diet and drugs which lower glucose levels The currently available oral hypoglycemic agents are not completely satisfactory since they may not offer complete blood glucose control or may provide a variety of undesirable side effects or they may elevate insulin concentrations to undesirable and dangerous levels Thus, the search for improved oral hypoglycemic agents is a continuing one.

As previously indicated, the compounds of this invention are all readily adapted to therapeutic use as oral hypoglycemic agents, in view of their ability to lower the blood sugar levels of diabetic subjects to a statistically significant degree. For instance, 2-methyl-4-(4-methylpiperazine 6H-7,8-dihydro thiapyrano [3,2-d]pyrimidine, a typical and preferred agent of the present invention, has been found to consistently lower blood sugar levels and improve glucose tolerance in either fasted or fed diabetic (i.e., hyperglycemic) mice to a statistically significant degree when given by the oral route of administration at dose levels ranging from 1 mg/kg to 100 mg/kg, respectively, without showing any toxic side effects. The other compounds of this invention also produce similar results. In general, these compounds are ordinarily administered at dosage levels ranging from about 1 mg to about 100 mg per kg of body weight per day, although variations will necessarily occur depending upon the condition and individual response of the subject being treated and the particular type of oral pharmaceutical formulation chosen.

Administration over time to obese, insulin resistant mice, resulted in a significant reduction in body weight.

In connection with the use of the compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia Additionally, lubricating agents such as magnesium stearate, sodium lauryl sulfate and talc are often very useful for tabletting purposes Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted or fed hyperglycemic mouse when tested therein for such purposes according to the procedures described by Saperstein et al. as submitted to the journal *Diabetes* and summarized as follows: Genetically obese mice (ob/ob) were fasted overnight. The compounds were administered orally via a stomach tube and each mouse serially bled from the orbital sinus at various times and the blood samples were analyzed for blood glucose When the effects of the compounds on blood glucose levels were to be determined, glucose was administered orally at a rate of 2 g per kg. 30 minutes after administration of the test compound Glucose in the blood was determined by the potassium ferricyanide potassium ferrocyanide oxidation reaction auto analyzer. The latter method measures directly the amount of glucose in the blood at any given time and from this, the maximum percent decrease in blood sugar can be readily calculated and reported as hypoglycemic activity per se. In this way, the present compounds are shown to markedly improve glucose tolerance of non-anesthetized hyperglycemic mice when administered to them at dose levels as low as 10 mg/kg orally and lower fasting blood glucose levels when adminstered at dose levels as low as 30 mg/kg orally.

What is claimed is:

1. A method for lowering the blood glucose levels of diabetic or insulin resistant obese patients which comprises orally administering to said patients an effective amount of the compound 7,8-Dihydro-2-methyl-4(4-methyl-1-piperazinyl)6H-thiapyranno(3,2-D)pyrimidine.

2. The method of claim 1 wherein the active compound is administered at a dose level of from 1 mg/kg to 100 mg/kg of body weight per day.

* * * * *